United States Patent
Kamachi et al.

(12)

(10) Patent No.: US 6,281,342 B1
(45) Date of Patent: Aug. 28, 2001

(54) PRADIMICIN COMPOUNDS

(75) Inventors: Hajime Kamachi, Urayasu; Minoru Hirano, Tachikawa; Shinji Masuyoshi, Yokohama, all of (JP)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 08/241,837

(22) Filed: May 12, 1994

Related U.S. Application Data

(62) Division of application No. 07/929,931, filed on Aug. 14, 1992, now Pat. No. 5,338,728.

(51) Int. Cl.[7] .................................................... C07H 1/00
(52) U.S. Cl. ...................... 536/18.5; 536/6.4; 536/17.9; 536/18.1
(58) Field of Search .................................. 536/6.4, 18.5, 536/17.9, 18.1

(56) References Cited

U.S. PATENT DOCUMENTS

| | | | |
|---|---|---|---|
| 3,796,709 | * | 3/1974 | Breuer et al. ................... 260/243 |
| 3,972,872 | * | 8/1976 | Hamanaka ..................... 260/239.1 |
| 4,152,433 | * | 5/1979 | Kamiya et al. ..................... 424/545 |

OTHER PUBLICATIONS

The Merck Index, ninth edition, (1976), pp. 1117–1118 No. 8407.*
Morrison et al, Organic Chemistry, third ed., (1973, pp. 763–764.*

* cited by examiner

*Primary Examiner*—Elli Peselev
(74) *Attorney, Agent, or Firm*—Samuel J. DuBoff; Thomas R. Savitsky

(57) ABSTRACT

Disclosed are novel pradimicin compounds which possess antifungal activity and, preferably, improved water solubility. The compounds of the invention are prepared by modifying the 4'-amino or 4'-alkylamino moieties of known pradimicin compounds.

2 Claims, No Drawings

PRADIMICIN COMPOUNDS

CROSS REFERENCE TO RELATED APPLICATION

This application is a divisional of application Ser. No. 07/929,931 filed Aug. 14, 1992, now U.S. Pat. No. 5,338,728.

BACKGROUND OF THE INVENTION

Pradimicin antibiotics such as pradimicin A, pradimicin C, pradimicin FA-1, and pradimicin FA-2, as well as certain derivatives thereof, are known in the art (see, for example, U.S. Pat. Nos. 4,870,165; 4,973,673, and 5,053,395).

The pradimicin antibiotics known in the art possess good antifungal activity. It would be desirable to have antifungal pradimicin derivatives which still have good antifungal activity but also have other important characteristics such as improved water solubility.

SUMMARY OF THE INVENTION

The present invention is directed to a compound having the formula:

(I)

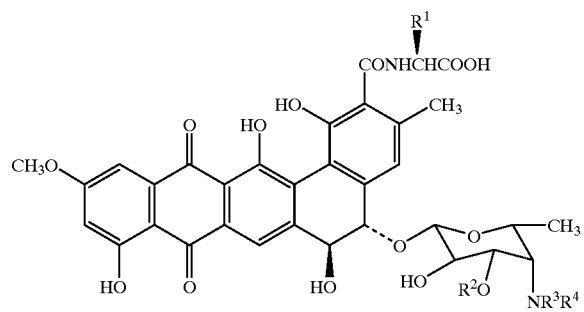

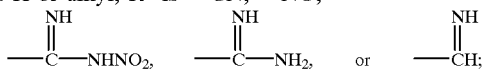

wherein $R^1$ is H, methyl, or hydroxymethyl, provided that when $R^1$ is methyl or hydroxymethyl, the resulting amino acid residue has the D configuration; $R^2$ is H or β-D-xylosyl; $R^3$ is H or alkyl; $R^4$ is —CN, —NO, $$-\underset{\underset{\|}{NH}}{C}-NHNO_2, \quad -\underset{\underset{\|}{NH}}{C}-NH_2, \quad or \quad -\underset{\underset{\|}{NH}}{C}H;$$

or a pharmaceutically acceptable salt thereof.

The present invention is also directed to a pharmaceutical composition comprising an antifungal effective amount of a compound of Formula I and a pharmaceutically acceptable carrier.

The present invention is further directed to a method for treating fungal infections in a mammalian host, preferably a human host, comprising administering to said host an antifungal effective dose of a compound of Formula I.

DETAILED DESCRIPTION OF THE INVENTION

As used herein, the term "alkyl" includes both straight and branched alkyl chains of one to six carbon atoms; "pharmaceutically acceptable salt" includes acid addition salts formed with, for example, hydrochloric acid, hydrobromic acid, sulfuric acid, phosphoric acid, nitric acid, acetic acid, tartaric acid, citric acid, methanesulfonic acid, succinic acid and the like; base salts with an alkali metal base such as sodium or potassium hydroxide, carbonate, and bicarbonate; and when possible internal salt (see, for example, "Pharmaceutical Salts", J. Pharm. Sci. 66(1):1–10 (1977)). The pharmaceutically acceptable salts of the invention can be prepared by any of the standard methods disclosed in the literature, for example, acid addition salts can be prepared by reacting a suitable basic compound of the invention with an organic or inorganic acid, preferably by contact in solution. Generally, the counter-ion of the salts of the invention does not contribute significantly to toxicity or pharmacological activity. Preferred alkyl groups have 1 to 3 carbon atoms and the most preferred alkyl group is methyl.

Preferred compounds of the invention are wherein $R^1$ is methyl or hydroxymethyl. It is also preferred that $R^2$ is β-D-xylosyl. It is further preferred that $R^3$ is H or methyl.

A preferred compound of the invention has the formula:

(II)

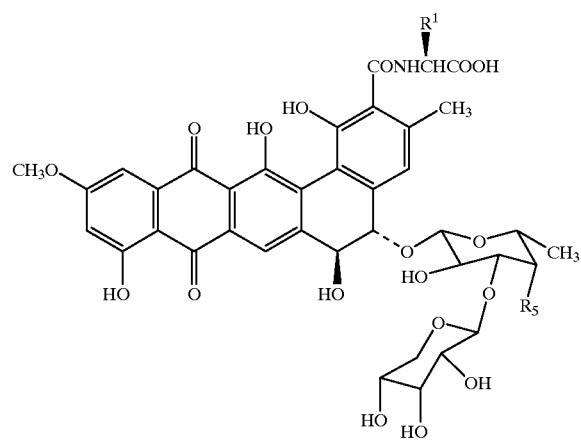

wherein $R^1$ is as defined above and $R^5$ is NHCN, N(CH$_3$)CN, N(CH$_3$)NO, NHCNH$_2$, NHC—NHNO or NHCH=NH, or a pharmaceutically acceptable salt thereof.

As used herein, the abbreviations "Me" shall mean methyl, "Et" shall mean ethyl, "Ac" shall mean acetyl, "Pd-C" shall mean palladium on carbon, "PBS" shall mean phosphate buffered saline.

Specific compounds of the invention referred to herein by the following alpha-numeric designations shall mean those compounds of Formula I having the following substitutions:

| Compound of the Invention | $R^1$ | $R^2$ | $R^3$ | $R^4$ |
|---|---|---|---|---|
| KHM-1 | methyl | β-D-xylosyl | methyl | —CN |
| KHM-2 | methyl | β-D-xylosyl | H | —CN |
| KHM-3 | hydroxy-methyl | β-D-xylosyl | methyl | —CN |
| KHM-4 | hydroxy-methyl | β-D-xylosyl | H | —CN |
| KHM-5 | hydroxy-methyl | β-D-xylosyl | methyl | NO |
| KHM-6 | methyl | β-D-xylosyl | methyl | NO |
| KHM-7 | methyl | β-D-xylosyl | H | C(=NH)NHNO$_2$ |
| KHM-8 | methyl | β-D-xylosyl | H | C(=NH)NH$_2$ |
| KHM-9 | methyl | β-D-xylosyl | H | CH=NH |

The starting material pradimicins A and C are produced by fermentation of *Actinomadura hibisca* strains P157-2 (ATCC 53557) and Q278-4 (ATCC 53646) as disclosed in U.S. Pat. No. 4,870,165 and the production of pradimicins FA-1 and FA-2 by mutant strains A2493 (ATCC 53815) and B0012 (ATCC 53816) capable of incorporating supplemented D-serine and derived from the parent strain P157-2 is disclosed in U.S. Pat. No. 4,973,673.

The 4'-cyanoamino and the 4'-guanidino derivatives of the invention can be synthesized from suitable pradimicin starting materials by treatment with a suitable silylation reagent such as N,O-bis(trimethylsilyl)acetamide ("BSA"), 1,1,1,3, 3,3-hexanethyldisilazane, chlorotrimethylsilane/ triethylamine, 1-(trimethylsilyl)imidazole, N-trimethylsilylacetamide, and the like followed by the substitution reactions. A preferred silylation reagent is BSA. The silylation reagent protects the hydroxyl groups and activates the 4'-amino group of pradimicins toward the substitution reactions at the same time. The treatment of the starting material with the silylation reagent can be carried out in an organic solvent such as dichloromethane, dichloroethane, tetrahydrofuran ("THF") toluene, diglyme, dimethylformamide ("DMF") or a mixture thereof for a time and temperature sufficient to activate the sugar amino group (4'-amino group). Typically, the activation reaction will be carried out between 5° C. and 50° C. for about 5 minutes to about 1 hour.

To prepare the 4'-cyanoamino derivatives, after activation the reaction mixture can be contacted with cyanogen bromide for a time and temperature sufficient to form the desired compound. Typically, a temperature of about room temperature to about 80° C. is employed, with room temperature being preferred, for about 2 to about 18 hours. After the silylated 4'-cyanoamino derivative is formed, the reaction mixture can be treated with a chloride reagent to remove the silyl moieties on the pradimicin molecules, such as hydrochloric acid in methanol. Fluoride reagents such as tetrabutylammonium fluoride and sodium fluoride can also be used for this purpose. The desired product can then be isolated from the reaction mixture by standard techniques known in the art such as column chromatography. For example, pradimicins A, C, FA-1, FA-2 (see U.S. Pat. Nos. 5,053,395, 4,870,165, 4,973,673, 4,992,425 and 4,960,755, all of which are incorporated herein by reference in their entirety) can be reacted with a silylation reagent in dichloromethane and then, the mixtures can be treated with cyanogen bromide at room temperature to afford, after treatment with hydrochloric acid in methanol and column chromatography, the 4'-cyanoamino derivatives of the invention (see Scheme 1).

To prepare the 4'-nitroguanidino derivatives more severe reaction conditions are required after activation. The silylation reagent-treated starting material is reacted with N-nitro-S-methylisothiourea for a time and temperature sufficient to form the desired products. Typically, a temperature of 50° C. to 100° C. is employed, with about 80° C. being preferred, for about 2 to about 18 hours. After the silylated 4'-nitroguanidine product is formed, the silyl moieties can be removed and the resulting desired product can be isolated in a similar manner as the 4'-cyanoamino derivatives. The solvent for the substitution reaction can be several organic solvents but is preferably the same as used in the activating reaction. If it is desired to prepare the 4'-guanidino derivative, the 4'-nitroguanidine compound can be deblocked by standard techniques to give the desired compound. A typical deblocking technique is to hydrogenate with gaseous hydrogen in the presence of a catalytic amount of a catalyst for a time and temperature sufficient to form the desired product. A temperature of about 10° C. to about room temperature can be employed, with room temperature being typical, for about 10 to about 20 hours. A typical catalyst is palladium on carbon (charcoal). The solvent for the deblocking procedure can be mixtures such as MeOH—HCl, EtOH—HCl, MeOH—AcOH, THF—AcOH (or HCl), dioxane-AcOH (or HCl), and the like. A preferred mixture is MeOH—HCl. To illustrate the reaction of silylation reagent-treated pradimicin C with N-nitro-S-methylisothiourea such reaction can be carried out in DMF at 80° C. for 2 hrs, after a work-up similar to the 4'-cyanoamino derivative, to give the 4'-(N-nitroguanidino) derivative which can be deblocked by catalytic hydrogenation to afford the 4'-guanidino derivative (see Scheme 2).

The 4'-amidino derivatives of the invention can be synthesized by catalytic hydrogenation of a suitable 4'-cyanoamino pradimicin starting material (see Scheme 3). The solvent for the hydrogenation can be aqueous organic acids such as acetic acid and citric acid; or diluted mineral acid in water (about 0.01N to about 0.5N) such as diluted HCl and diluted $H_2SO_4$. An aqueous acetic acid solution is preferred. A temperature of about 0° C. to about room temperature can be employed with room temperature being typical, for about 30 minutes to about 2 hours.

The 4'-nitrosoamino derivatives of the mixture can be prepared by treatment of a suitable pradimicin starting material such as pradimicin A or pradimicin FA-1, with sodium nitrite in a suitable solvent such as aqueous acetic acid (see Scheme 4).

Reaction schemes 1–4 illustrate synthesis of certain compounds of the invention. Other compounds of the invention not specifically illustrated can be synthesized utilizing similar procedures with the appropriate starting materials.

Scheme 1

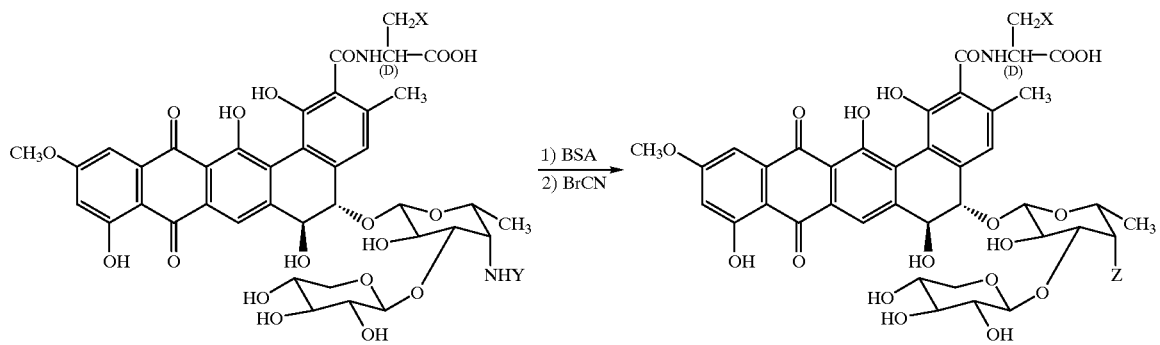

| Starting Material | X | Y | Compound of the Invention | X | Z |
|---|---|---|---|---|---|
| Pradimicin A | H | Me | KHM-1 | H | NMeCN |
| Pradimicin C | H | H | KHM-2 | H | NHCN |
| Pradimicin FA-1 | OH | Me | KHM-3 | OH | NMeCN |
| Pradimicin FA-2 | OH | H | KHM-4 | OH | NHCN |

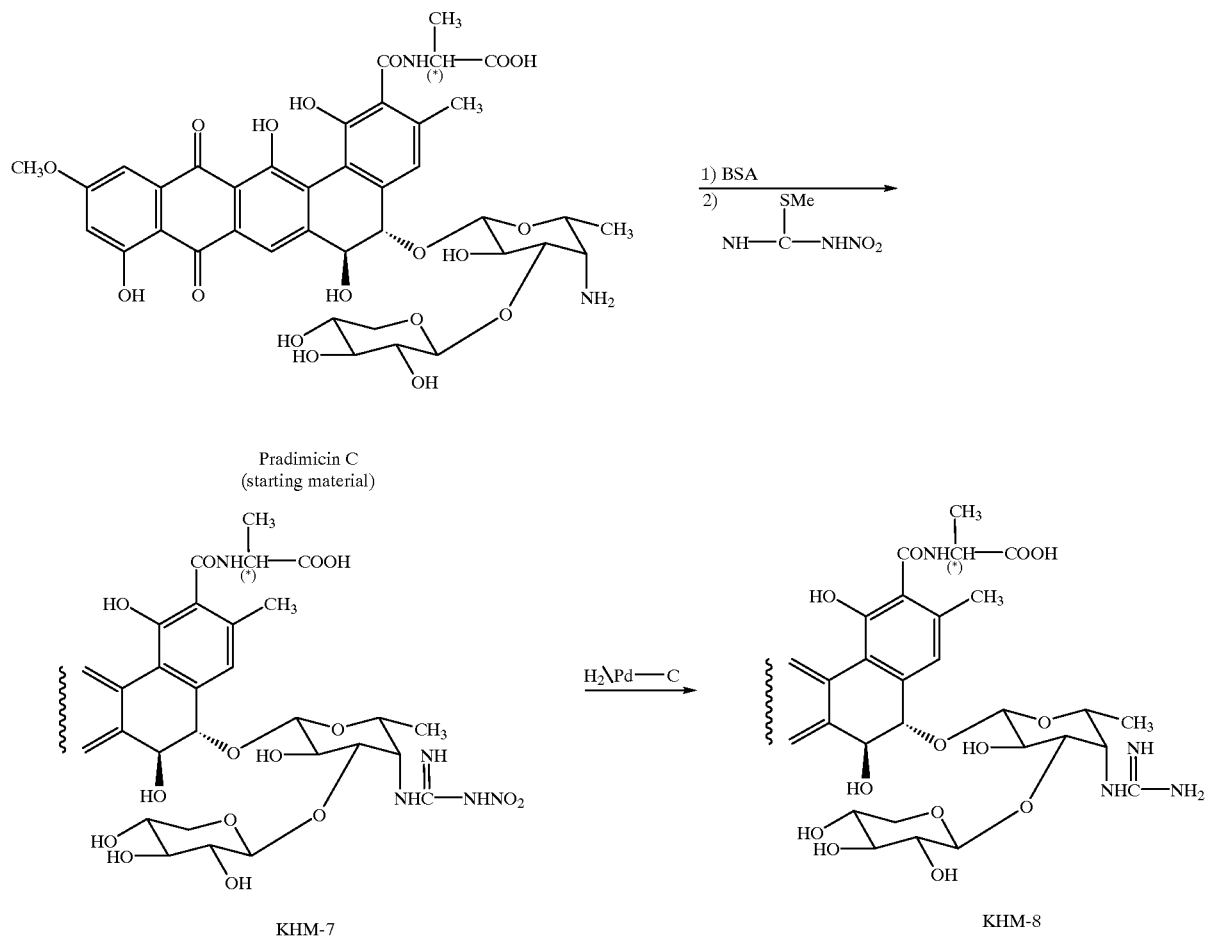
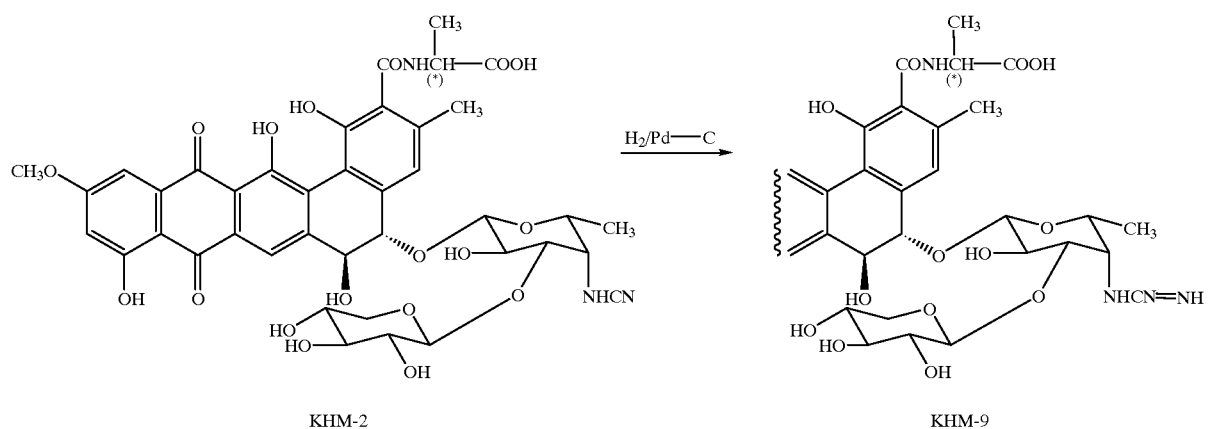

Scheme 4

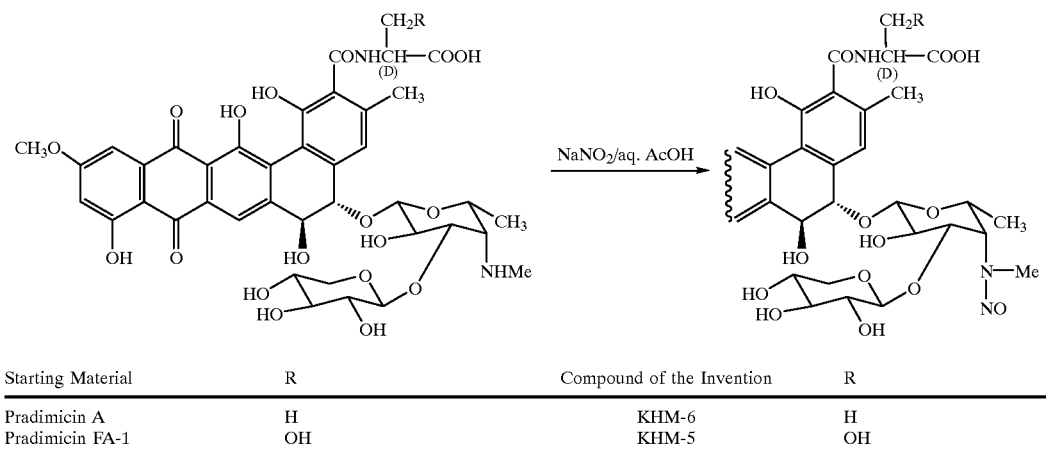

| Starting Material | R | Compound of the Invention | R |
|---|---|---|---|
| Pradimicin A | H | KHM-6 | H |
| Pradimicin FA-1 | OH | KHM-5 | OH |

Thus, in view of the foregoing, the present invention is also directed to the following processes:

A process for preparing a 4'-cyanoamino pradimicin compound comprising contacting a 4'-amino or 4'-alkylamino pradimicin compound in a suitable organic solvent with a silylation reagent under conditions sufficient to activate the 4'-amino group or the 4'-alkylamino group, followed by contacting the activated compound with cyanogen bromide under conditions sufficient to form a silylated 4'-cyanoamino pradimicin derivative, followed by removal of the silyl moieties to result in formation of the desired 4'-cyanoamino derivative; a process for preparing a 4'-nitroguanidino pradimicin compound comprising contacting a 4'-amino or 4'-alkylamino pradimicin compound in a suitable solvent with a silylation reagent under conditions sufficient to activate the 4'-amino group or the 4'-alkylamino group, followed by contacting the activated compound with N-nitro-S-methylisothiourea under conditions sufficient to form a silylated 4'-guanidino pradimicin, followed by removal of the silyl moities to result in formation of the desired 4'-guanidino pradimicin compound; a process for preparing a 4'-nitroguanidino pradimicin compound comprising contacting a 4'-nitroguanidino pradimicin compound with gaseous hydrogen in a suitable solvent in the presence of a catalytic amount of a catalyst under conditions to form the desired 4'-nitroguanidine compound; a process for preparing a 4'-amidino pradimicin compound comprising contacting a 4'-cyanoamino pradimicin compound with gaseous hydrogen in a suitable solvent under conditions to form the desired 4'-amidino compound; and a process for preparing a 4'-nitrosoamino compound comprising contacting a 4'-alkylamino compound with sodium nitrite in a suitable solvent under conditions to form the desired 4'-nitrosoamino compound.

The compounds of the present invention have good antifungal activity against a wide variety of fungal species such as Candida, Tichophyton, Aspergillus, Saccharomyces and Cryptococcus species.

The amount of the compound of the invention administered to a patient would depend in part on the age, weight, and general condition of the patient. Typically, a patient would be closely monitored by a physician who could determine if the dosage amount or regimen of compound being administered was effective and well tolerated. The compound of the invention would be administered either alone or admixed with a pharmaceutically acceptable carrier.

An effective daily dose of the compound of the invention ranges from about 2.5 to about 100 mg/kg of body weight of the patient.

For preparing pharmaceutical compositions from the compound of this invention, inert, pharmaceutically acceptable carriers can be either solid or liquid. Solid form preparations include powders, tablets, dispersible granules, capsules, cachets, and suppositories.

A solid carrier can be one or more substances which may also act is diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool solidly.

Suitable carriers for powders and tablets are magnesium carbonate, magnesium stearate, talc, lactose, sugar, pectin, dextrin, starch, tragacanth, methyl cellulose, sodium carboxymethyl cellulose, cellulose esters such as cellulose acetate phthalate, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

For topical administration, the compound may be incorporated into lotions, ointments, gels, creams, salves, tinctures, and the like.

Liquid form preparations include solutions suitable for oral or parenteral administration; or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions for injection or infusion may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules and powders in vials or ampules. The unit dosage form can also be capsule, cachet, or tablet itself, or it can be the appropriate number of any of these packaged forms.

The compounds of the invention have good water solubility. Typically, the water solubility is greater than 10 mg/ml when measured at neutral pH in PBS containing $Ca^{2+}/Mg^{2+}$, preferably greater than 20 mg/ml.

The following examples are to illustrate the invention but should not be interpreted as a limitation thereof.

EXAMPLE 1

KHM-1: 4'-N-Cyanogradimicin A

Cyanogen bromide (180 mg, 1.7 mmol) was added to a mixture of pradimicin A (88 mg, 0.104 mmol) and BSA (0.5 ml, 2.02 mmol) in dichloromethane (2 ml) and the mixture was stirred overnight at room temperature. After removal of the solvent, MeOH (2 ml) and 1 N hydrochloric acid (1 ml) was added and the mixture was chromatographed on a column of Cosmosil 75$C_{18}$-OPN (Nacalai Tesque, Inc., 100 g). The column was eluted with water and 10–40% acetonitrile-water successively. The eluate was collected in fractions, which were monitored by HPLC. The fractions containing the desired product were combined, concentrated in vacuo and freeze-dried to give 73 mg (81%) of the title compound as a light red amorphous powder. MP>250° C. (dec.); $IR_{max}$ KBr $cm^{-1}$ 2200, 1720, 1600, 1290, 1165; Mass (FAB) m/z 866 (M+H)$^+$; UV $\lambda_{max}$1/100N NaOH nm($\epsilon$) 319 (14800), 496 (13900); $^1$H NMR (DMSO-$d_6$)$\delta$ ppm 1.18 (3H,d, J=7 Hz, 5'-$CH_3$), 1.33 (3H,d, J=7 Hz, 17-$CH_3$), 2.28 (3H,s, 3-$CH_3$), 3.00 (3H, s, 4'-$NCH_3$), 3.74 (1H,dd, J=5 & 11 Hz, 5"-H), 3.95 (3H,s, $OCH_3$), 4.39 (1H,q, J=7 Hz, 17-H), 4.41 (1H,d, J=10 Hz, 5-H), 4.50 (1H,br d, J=10 Hz, 6-H), 4.64 (1H,d, J=8 Hz, 1'-H), 6.89 (1H,d, J=2 Hz, 10-H), 7.19 (1H,s, 4-H), 7.26 (1H,s, 12-H), 8.00 (1H,s, 7-H), 8.59 (1H,s, 16-NH).

EXAMPLE 2

KHM-2: 4'-N-Cyanopradimicin C

Cyanogen bromide (180 mg, 1.7 mmol) was added to a mixture of pradimicin C (67 mg, 0.081 mmol) and BSA (0.5 ml, 2.02 mmol) in dichloromethane (2 ml) and the mixture was stirred overnight at room temperature. After removal of the solvent, MeOH (2 ml) and 1 N hydrochloride acid (1 ml) was added and the mixture was chromatographed on a column of Cosmosil 75$C_{18}$-OPN (Nacalai Tesque, Inc. 100 g). The column was eluted with water and 10–40% acetonitrile successively. The eluate was collected in fractions, which were monitored by high performance liquid chromatography (HPLC). The fractions containing the desired product were combined, concentrated in vacuo and freeze-dried to give 48 mg (79%) of the title compound as a light red amorphous powder. MP 220–230° C. (dec.); $IR_{max}$ $\nu$KBr $cm^{-1}$ 2210, 1720, 1620, 1300, 1060; Mass (FAB) m/z 852 (M+H)$^+$; UV $\lambda_{max}$1/100N NaOH nm($\epsilon$) 319 (14800), 496 (15400); $^1$H NMR (DMSO-$d_6$)$\delta$ppm 1.15 (3H,d, J=7 Hz, 5' $CH_3$), 1.33 (3H,d, J=7 Hz, 17-$CH_3$), 2.29 (3H,s, 3-$CH_3$), 3.93 (3H,s, $OCH_3$), 4.39 (1H,q, J=7 Hz, 17-H), 4.48 (1H,d, J=10 Hz, 5-H), 4.52 (1H,br d, J=10 Hz, 6-H), 4.64 (1H, d, J=8 Hz, 1'-H), 6.73 (1H,d, J=12 Hz, NHCH), 6.87 (1H,d, J=2 Hz, 10-H), 7.11 (1H,s, 4-H), 7.25 (1H,d, J=2 Hz, 12-H), 7.93 (1H, s, 7-H), 8.62 (1H,d, J=7 Hz, 16-NH).

EXAMPLE 3

KHM-9: 4'-Amidinopradimicin C

A mixture of 4'-cyanoaminopradimicin C (BMY-29295, 35 mg, 0.041 mmol) and 10% palladium on charcoal (10 mg) in 25% aqueous acetic acid was hydrogenated overnight under atmospheric pressure. HPLC showed that there were two products generated in this reaction. One of them, (Retention time, 9.9 min, column SSC-ODS-226, solvent 30% acetonitrile in pH 3.5 buffer) was coincident with 4'-carbamoylaminopradimicin C and the other (Retention time, 6.9 min) was the desired compound.

The mixture was chromatographed on a column of Cosmosil 75$C_{18}$-OPN (Nacalai Tesque, Inc., 100 g) and the column was eluted with water and 10–40% acetonitrile successively. The eluate was collected in fractions, which were monitored by HPLC. The fractions containing the 4'-carbamoylamino pradimicin C were combined, concentrated in vacuo and freeze-dried to give 10 mg (27%) of the product as a light red amorphous powder. The column was then eluted with 1/1000 N hydrochloric acid-acetonitrile (80:20–60:40) to give 5 mg (14%) of the title compound as a light red powder by a similar work-up. MP 220–230° C. (dec.); IR $\nu_{max}$KBr $cm^{-1}$ 1700, 1605, 1290, 1160; Mass (FAB) m/z 854 (M+H)$^+$; UV $\lambda_{max}$1/100N NaOH nm($\epsilon$) 319 (14100), 496 (14900); $^1$H NMR (DMSO -$d_6$) $\delta$ ppm 1.09 (3H,d, J=7 Hz, 5'-$CH_3$), 1.34 (3H,d, J=7 Hz, 17-$CH_3$), 2.29 (3H,s, 3-$CH_3$), 3.94 (3H,s, $OCH_3$), 4.39 (1H,q, J=7 Hz, 17-H), 4.48 (1H,d, J=10 Hz, 5-H), 4.50 (2H,br, 5- &6-H), 6.83 (1H,s, 10-H), 7.02 (1H,s, 4-H), 7.22 (1H,s, 12-H), 7.82 (1H,s, 7-H), 7.90 (1H,s, NHC$\underline{H}$=NH), 8.68 (1H,br, 16-NH).

EXAMPLE 4

KHM-3: 4'-Cyanooradimicin FA-1

Cyanogen bromide (180 mg, 1.7 mmol) was added to a mixture of pradimicin FA-1 (88 mg, 0.102 mmol) and BSA (0.5 ml, 2.02 mmol) in dichloromethane (2 ml) and the mixture was stirred overnight at room temperature. After removal of the solvent, MeOH (2 ml) and 1 N hydrochloric acid (1 ml) was added and the mixture was chromatographed on a column of Cosmosil 75$C_{18}$-OPN (Nacalai Tesque, Inc., 100 g). The column was eluted with water and 10–40% acetonitrile-water successively. The eluate was collected in fractions, which were monitored by HPLC. The fractions containing the desired product were combined, concentrated in vacuo and freeze-dried to give 72 mg (80%) of the title compound as a light red amorphous powder. MP 220–230° C. (dec.); IR $\nu_{max}$KBr $cm^{-1}$ 2200, 1720, 1600, 1290, 1165; Mass (FAB) m/z 882 (M+H)$^+$; UV $\lambda_{max}$1/100NNaOH nm($\epsilon$) 319 (14300), 496 (13700); $^1$H NMR (DMSO-$d_6$) $\delta$ ppm 1.18 (3H,d, J=7 Hz, 5'-$CO_3$), 2.30 (3H,s, 3-$CH_3$), 3.00 (3H,s, 4'-$NCH_3$), 3.95 (3H,s, $OCH_3$), 4.42 (1H,d, J=10 Hz, 5-H), 4.52 (1H, br d, J=10 Hz, 6-H), 4.64 (1H,d, J=8 Hz, 1'-H), 6.91 (1H,d, J=2 Hz, 10-H), 7.22 (1H,s, 4-H), 7.27 (1H,d, J=2 Hz, 12-H), 8.25 (1H,s, 7-H), 8.34 (1H,d, J=7 Hz, 16-NH).

EXAMPLE 5

KHM-4: 4'-N-Cyanopradimicin FA2

Cyanogen bromide (180 mg, 1.7 mmol) was added to a mixture of pradimicin FA-1 (90 mg, 0.107 mmol) and BSA (0.5 ml, 2.02 mmol) in dichloromethane (2 ml) and the mixture was stirred overnight at room temperature. After removal of the solvent, MeOH (2 ml) and 1 N hydrochloric acid (1 ml) was added and the mixture was chromatographed on a column of Cosmosil 75C$^{18}$-OPN (Nacalai Tesque, Inc., 100 g). The column was eluted with water and 10–40% acetonitrile-water successively. The eluate was collected in fractions, which were monitored by HPLC. The fractions containing the desired product were combined, concentrated in vacuo and freeze-dried to give 59 mg (64%) of the title compound as a light red amorphous powder. MP 205–220° C. (dec.); IR $v_{max}$KBr cm$^{-1}$ 2210, 1720, 1600, 1290, 1165; Mass (FAB) m/z 868 (M+H)$^+$; UV $\lambda_{max}$1/100N NaOH nm($\epsilon$) 319 (14900), 498 (14300); $^1$H NMR (DMSO-d$_6$) $\delta$ ppm 1.15 (3H,d, J=7 Hz, 5'-CH$_3$), 2.32 (3H,s, 3-CH$_3$), 3.95 (3H,s, OCH$_3$), 4.39 (1H,d, J=7 Hz, 1"1-H), 4.46 (1H,m, 17-H), 4.53 (1H, br d, J=10 Hz, 6-H), 4.65 (1H,d, J=8 Hz, 1'-H), 6.73 (1H, J=12 Hz, NHCN), 6.90 (1H,s, 10-H), 7.13 (1H,s, 4-H), 7.26 (1H,s, 12-H), 7.98 (1H,s, 7-H), 8.39 (1H,d, J=7 Hz, 16-NH).

EXAMPLE 6

KHM-6: 4'-N-Nitrosopradimicin A

Sodium nitrite (1 M aqueous solution, 0.5 ml) was added dropwise to a stirred solution of pradimicin A (100 mg, 0.12 mmol) in 0.25 M aqueous acetic acid (10 ml). The mixture was stirred for 2 hr at room temperature and chromatographed on a column of Cosmosil 75C$_{18}$-OPN (Nacalai Tesque, Inc., 100 g). The column was eluted with water and 10–50% acetonitrile successively. The eluate was collected in fractions, which were monitored by HPLC. The fractions containing the desired product were combined, concentrated in vacuo and freeze-dried to give 75 mg (72%) of the title compound as a light red amorphous powder. MP 230–240° C. (dec.); IR $v_{max}$KBr cm$^{-1}$ 1720, 1600, 1450, 1295, 1160, 1060; Mass (FAB) m/z 870 (M+H)$^+$; UV $\lambda_{max}$1/100N NaOH nm($\epsilon$) 320 (14100), 498 (14000); $^1$H NMR (DMSO-d$_6$) $\delta$ ppm 0.98 (3H,d, J=7 Hz, 5'-CH$_3$), 1.33 (3H,d, J=7 Hz, 17-CH$_3$), 2.29 (3H,s, 3-CH$_3$), 3.15 (3H,s, 4'-NCH$_3$), 3.67 (1H,dd, J=5 & 11 Hz, 5"-H), 3.95 (3H,s, OCH$_3$), 4.40 (1H,q, J=7 Hz, 17-H), 4.47 (1H,d, J=7 Hz, 1"-H), 4.54 (2H, br s, 5,6-H), 4.81 (1H,d, J=8 Hz, 1'-H), 6.92 (1H,d, J=2 Hz, 10-H), 7.40 (1H,s, 4-H), 7.28 (1H,d, J=2 Hz, 12-H), 8.20 (1H,s, 7-H), 8.59 (1H,d, J=7 Hz, 16-NH).

EXAMPLE 7

KHM-5: 4'-N-Nitrosopradimicin FA-1

Sodium nitrite (1 M aqueous solution, 0.5 ml) was added dropwise to a stirred solution of pradimicin FA-1 (100 mg, 0.12 mmol) in 0.25 M aqueous acetic acid (10 ml). The mixture was stirred for 2 hr at room temperature and chromatographed on a column of Cosmosil 75C$_{18}$-OPN (Nacalai Tesque, Inc., 100 g). The column was eluted with water and 10–50% acetonitrile successively. The eluate was collected in fractions, which were monitored by HPLC. The fractions containing the desired product were combined, concentrated in vacuo and freeze-dried to give 55 mg (53%) of the title compound as a light red amorphous powder. MP 220–230° C. (dec.); IR $v_{max}$KBr cm$^{-1}$ 1720, 1600, 1440, 1340, 1295, 1160, 1060; Mass (FAB) m/z 886 (M+H)$^+$; UV $\lambda_{max}$1/100N NaOH nm($\epsilon$) 319 (14700), 497 (14100); $^1$H NMR (DMSO-d$_6$) $\delta$ ppm 0.98 (3H,d, J=7 Hz, 5'-CH$_3$), 2.31 (3H,s, 3-CH$_3$), 3.16 (3H,s, N—CH$_3$), 3.68 (1H,dd, J=5 & 11 Hz, 5"-H), 3.74 (2H,m, CH$_2$O), 3.95 (3H,s, OCH$_3$), 4.47 (1H,d, J=7 Hz, 1"-H), 4.60 (1H,m, 17-H), 4.51 (1H,d, J=10 Hz, 5-H), 4.54 (1H,br d, J=10 Hz, 6-H), 4.81 (1H,d, J=8 Hz, 1'-H), 6.85 (1H,d, J=2 Hz, 10-H), 6.99 (1H,s, 4-H), 7.23 (1H,d, J=2 Hz, 12-H), 7.93 (1H,s, 7-H), 8.44 (1H,d, J=7 Hz, 16-NH).

EXAMPLE 8

KHM-7: 4'-Nitroquanidinopradimicin C

N-Nitro-S-methylisothiourea (150 mg, 1.24 mmol) was added to a mixture of pradimicin A (100 mg, 0.12 mmol) and BSA (0.5 ml, 2.02 mmol) in DMF (2 ml) and the mixture was heated at 80° C. for 2 hours. After removal of the solvent, MeOH (2 ml) and 1 N hydrochloric acid (1 ml) was added and the mixture was chromatographed on a column of Cosmosil 75C$_{18}$-OPN (Nacalai Tesque, Inc., 100 g) and the column was eluted with water and 10–40% acetonitrile successively. The eluate was collected in fractions, which were monitored by HPLC. The fractions containing the desired product were combined, concentrated in vacuo and freeze-dried to give 69 mg (63%) of the title compound as a light red amorphous powder. MP 220–230° C. (dec); IR $v_{max}$KBr cm$^{-1}$ 1720, 1600, 1290, 1160, 1050; Mass (FAB) m/z 914 (M+H)$^+$; UV $\lambda_{max}$1/100N NaOH nm($\epsilon$) 316 (1600), 497 (14700); $^1$H NMR (DMSO-d$_6$) $\delta$ ppm 1.06 (3H,d, J=7 Hz, 5'-CH$_3$), 1.34 (3H,d, J=7 Hz, 17-CH$_3$), 2.32 (3H,s, 3-CH$_3$), 3.95 (3H,s, OCH$_3$), 4.40 (1H,q, J=7 Hz, 17-H), 4.44 (1H,d, J=7 Hz, 1"-H), 4.50 (1H,d, J=10 Hz, 5-H), 4.60 (1H,br d, J=10 Hz, 6-H), 4.76 (1H,d, J=8 Hz, 1'-H), 6.91 (1H,s, 10-H), 7.11 (1H,s, 4-H), 7.28 (1H,s, 12-H), 8.02 (1H,s, 7-H), 8.59 (1H,d, J=7 Hz, 16-NH).

EXAMPLE 9

KHM-8: 4'-Guanidinopradimicin C

A mixture of 4'-nitroguanidinopradimicin C (50 mg, 0.055 mmol) and 10% palladium on charcoal (20 mg) in 1 N HCl-MeOH (1:10, 5 ml) was hydrogenated overnight under atmospheric pressure. The mixture was chromatographed on a column of Cosmosil 75C$_{18}$-OPN (Nacalai Tesque, Inc. 100 g) and the column was eluted with water and then with 1/1000 N hydrochloric acid—acetonitrile (80:20–60:40) successively. The eluate was collected in fractions, which were monitored by HPLC. The fractions containing the desired product were combined, concentrated in vacuo and freeze-dried to give 18 mg (38%) of the title compound as a light red powder in a similar work-up. MP 220–230° C. (dec.); IR $v_{max}$KBr cm$^{-1}$ 1720, 1605, 1290, 1150; Mass (FAB) m/z 869 (M+H)$^+$; UV $\lambda_{max}$1/100NNaOH nm($\epsilon$) 318 (14700), 498 (14100); $^1$H NMR (DMSO -d$_6$) $\delta$ ppm 1.08 (3H,d, J=7 Hz, 5'-CH$_3$), 1.34 (3H,d, J=7 Hz, 17-CH$_3$), 2.30 (3H,s, 3-CH$_3$), 3.95 (3H,s, OCH$_3$), 4.40 (1H,q, J=7 Hz, 17-H), 4.43 (1H,d, J=7 Hz, 141 -H), 4.55 (2H, br s, 5-H, 6-H), 4.76 (1H,d, J=8 Hz, 1'-H), 6.85 (1H,s, 10-H), 7.04 (1H,s, 4-H), 7.24 (1H,s, 12-H), 7.88 (1H,s, 7-H), 8.65 (1H,d, J=7 Hz, 16-NH).

EXAMPLE 10

Biological Activity and Solubility

In vitro and in vivo antifungal activities of the pradimicin derivatives of the invention.

In vitro Susceptibility Testing

Minimum inhibitory concentrations (MICs) of nine 4'-N-substituted pradimicin derivatives were determined by twofold agar dilution method on phosphate-buffered yeast morphology agar (YMA, pH 7.0, Difco Laboratories). A 5-µl of fungal cell suspension containing $2\times10^6$ cells/ml ($2\times10^7$ cells/ml for *Trichophyton mentagrophytes*) were spotted on the surface of the agar plates containing test compound. MICs were recorded after 40-hour incubation at 28° C. except for *T. mentagrophytes*, which required 60-hour incubation to produce visually evaluable growth on the drug-free control plates and were defined as the lowest antibiotic concentrations showing no growth or less than five discrete colonies per spot. The MICs are summarized in Table 1.
Experimental Fungal Infections in Mice The in vivo therapeutic efficacies of seven 4'-N-substituted pradimicin derivatives, KHM-1, KHM-2, KHM-3, KHM-4, KHM-5, KHM-6 and KHM-7 were evaluated in the mouse infected with Candida albicans A9540 and *Aspergillus fumigatus* IAM 2034. Groups of five specific-pathogen-free male ICR mice weighing 20–25 g at each dose level were intravenously infected with approximately 10 times the 50% lethal dose of *C. albicans* A9540 ($1\times10^6$ cells/mouse) or *A. fumigatus* IAM 2034 ($1\times10^7$ cells/mouse). Immediately after the fungal infection, test compounds dissolved with 10% DMSO in distilled water were intravenously given to the mouse at the dosed volume of 0.1 ml/10 g of body weight. The therapeutic efficacy was demonstrated as the 50% protection dose ($PD_{50}$) which was calculated by the method of Van der Waerden (Arch. Exp. Pathol. Pharmakol. 195 389–412, 1940) from the survival rate recorded on 20th day post-infection. Untreated control animals died 7 to 13 days post-infection. These results are summarized in Table 2.

TABLE 1-1

Spectra of in vitro antifungal activity for 4'-N-substituted pradimicin derivatives, pradimicins A, C, FA-1 and FA-2

| Test Organism | MIC (µg/ml) | | | | | |
| --- | --- | --- | --- | --- | --- | --- |
| | KHM-1 | KHM-2 | KHM-3 | KHM-4 | KHM-5 | KHM-6 |
| *Saccharomyces cerevisiae* ATCC 9763 | 1.6 | 3.1 | 1.6 | 3.1 | 3.1 | 3.1 |
| *Candida albicans* IAM 4888 | 3.1 | 3.1 | 6.3 | 6.3 | 6.3 | 6.3 |
| *Candida albicans* A9540 | 3.1 | 3.1 | 6.3 | 6.3 | 6.3 | 6.3 |
| *Candida albicans* ATCC 38247 | 1.6 | 1.6 | 3.1 | 3.1 | 3.1 | 1.6 |
| *Candida albicans* ATCC 32354 | 3.1 | 3.1 | 6.3 | 3.1 | 6.3 | 3.1 |
| *Candida albicans* 83-2-14 | 3.1 | 6.3 | 6.3 | 6.3 | 6.3 | 6.3 |
| *Candida tropicalis* 85-8 | 12.5 | 12.5 | 12.5 | 12.5 | 12.5 | 12.5 |
| *Candida tropicalis* IFO 10241 | 12.5 | 12.5 | 12.5 | 12.5 | 12.5 | 12.5 |
| *Cryptococcus neoformans* D49 | 3.1 | 3.1 | 6.3 | 6.3 | 3.1 | 1.6 |
| *Cryptococcus neoformans* IAM 4514 | 3.1 | 1.6 | 6.3 | 3.1 | 3.1 | 1.6 |
| *Aspergillus fumigatus* IAM 2034 | 12.5 | 3.1 | 25 | 6.3 | 3.1 | 3.1 |
| *Trichophyton mentagrophytes* #4329 | 25 | 12.5 | 50 | 12.5 | 6.3 | 3.1 |

Medium: yeast morphology agar + 1/15 M phosphate buffer (pH 7.0)
Incubation conditions: 28° C., 40 hours (*C. albicans* ATCC 38247 & *T. mentagrophytes* #4329: 28° C., 60 hours).

TABLE 1-2

Spectra of in vitro antifungal activity for 4'-N-substituted pradimicin derivatives, pradimicins A, C, FA-1 and FA-2

| Test Organism | MIC (µg/ml) | | | | | | |
| --- | --- | --- | --- | --- | --- | --- | --- |
| | KHM-7 | KHM-8 | KHM-9 | Padimicin A | Pradimicin C | Pradimicin FA-1 | Pradimicin FA-2 |
| *Saccharomyces cerevisiae* ATCC 9763 | 3.1 | 25 | 1.6 | 6.3 | 6.3 | 1.6 | 1.6 |
| *Candida albicans* IAM 4888 | 3.1 | 12.5 | 6.3 | 6.3 | NT | NT | NT |
| *Candida albicans* A9540 | 3.1 | 12.5 | 12.5 | 12.5 | 25 | 6.3 | 6.3 |
| *Candida albicans* ATCC 38247 | 1.6 | NT | NT | 3.1 | 3.1 | 1.6 | 1.6 |
| *Candida albicans* ATCC 32354 | 3.1 | 12.5 | 6.3 | 3.1 | 6.3 | 3.1 | 3.1 |
| *Candida albicans* 83-2-14 | 6.3 | >100 | 12.5 | >100 | 50 | 6.3 | 6.3 |
| *Candida tropicalis* 85-8 | 12.5 | >100 | 50 | >100 | 100 | 6.3 | 6.3 |
| *Candida tropicalis* IFO 10241 | 12.5 | >100 | >100 | >100 | 100 | 6.3 | 6.3 |
| *Cryptococcus neoformans* D49 | 3.1 | 6.3 | 12.5 | 1.6 | 0.8 | 1.6 | 1.6 |
| *Cryptococcus neoforinans* IAM 4514 | 1.6 | 6.3 | 3.1 | 1.6 | 0.8 | 0.8 | 1.6 |
| *Aspergillus fumigatus* IAM 2034 | 3.1 | 3.1 | 1.6 | 1.6 | 3.1 | 1.6 | 1.6 |
| *Trichophyton mentagrophytes* #4329 | 3.1 | 3.1 | 3.1 | 3.1 | 3.1 | 1.6 | 3.1 |

NT: Not tested,
Medium: Yeast morphology agar + 1/15 phosphate buffer (pH 7.0).
Incubation conditions: 28° C., 40 hours (*C. albicans* ATCC 38247 & *T. mentagrophytes* #4329: 28° C., 60 hours).

TABLE 2

In vivo Activity of 4'-N-Substituted
Pradimicin Derivatives, Pradimicins A, C, FA-1 and FA-2
Against Candida and Aspergillus Systemic Infections In Mice

| Compound | Dose (mg/kg, iv) | *C. albicans* A954D S/T* | PD50 (mg/kg, iv) | *A. fumigatus* IAM2034 S/T* | PD50 (mg/kg, iv) |
|---|---|---|---|---|---|
| KHM-2 | 50 | 5/5 | 13 (11–17)** | 1/5 | >50 |
|  | 25 | 4/5 |  | 0/5 |  |
|  | 12.5 | 3/5 |  | 2/5 |  |
|  | 6.3 | 1/5 |  | 0.5 |  |
| KHM-2 | 50 | 5/5 | 13 (10–17) | 3/5 | 27 (23–32)** |
|  | 25 | 4/5 |  | 2/5 |  |
|  | 12.5 | 2/5 |  | 1/5 |  |
|  | 6.3 | 1/5 |  | 0/5 |  |
| KHM-3 | 50 | 2/5 | >50 | 0/5 | >50 |
|  | 25 | 0/5 |  | 0/5 |  |
|  | 12.5 | 0/5 |  | 0/5 |  |
| KHM-4 | 50 | 4/5 | 20 (16–25) | 0/5 | >50 |
|  | 25 | 3/5 |  | 0/5 |  |
|  | 12.5 | 1/5 |  | 0/5 |  |
|  | 6.3 | 0/5 |  | 0/5 |  |
| KHM-5 | 50 | 2/5 | >50 | 2/5 | >50 |
|  | 25 | 0/5 |  | 0/5 |  |
|  | 12.5 | 1/5 |  | 0/5 |  |
| KHM-6 | 50 | 4/5 | 27 (22–33) | 2/5 | >50 |
|  | 25 | 1/5 |  | 0/5 |  |
|  | 12.5 | 1/5 |  | 2/5 |  |
|  | 6.3 | 0/5 |  | 0/5 |  |
| KHM-7 | 50 | 4/5 | 12 (8.7–16) | 1/5 | >50 |
|  | 25 | 3/5 |  | 0/5 |  |
|  | 12.5 | 3/5 |  | 2/5 |  |
|  | 6.3 | 2/5 |  | 1/5 |  |
| Pradimicin A | 50 | 5/5 | 10 (8.8–12) | 5/5 | 23 (20–28) |
|  | 25 | 5/5 |  | 3/5 |  |
|  | 12.5 | 4/5 |  | 1/5 |  |
|  | 6.3 | 0/5 |  | 0/5 |  |
| Pradimicin C | 50 | 0/5 | (tox) |  |  |
|  | 25 | 5/5 | 13 (11–16) | Not tested |  |
|  | 12.5 | 2/5 |  |  |  |
|  | 6.3 | 2/5 |  |  |  |
| Pradimicin FA-1 | 50 | 5/5 | 18 (15–22) | 4/5 | 27 (23–32) |
|  | 25 | 4/5 |  | 2/5 |  |
|  | 12.5 | 1/5 |  | 1/5 |  |
|  | 6.3 | 0/5 |  | 0/5 |  |
| Pradimicin FA-2 | 50 | 5/5 | 7.7 (1.6–9.6) |  |  |
|  | 25 | 5/5 |  | Not tested |  |
|  | 12.5 | 4/5 |  |  |  |
|  | 6.3 | 2/5 |  |  |  |

*No. of survivors/tested.
**95% Confidence limits.

Solubility

The solubilities of pradimicin derivatives of the invention are shown in Table 3 along with comparative data for other pradimicins. Table 3 also summarizes some biological data.

TABLE 3

| Compound | MIC (µg/ml, YMA)[1] | | | | PD$_{50}$ (mice) (iv, mg/kg) | | Solubility[2] (mg/ml) |
|---|---|---|---|---|---|---|---|
|  | Ca-4 | Cn-2 | Af-3 | TM-4 | Ca-4 | Af-3 |  |
| KHM-1 | 3.1 | 3.1 | 12.5 | 25 | 13 | >50 | NT |
| KHM-2 | 3.1 | 1.6 | 3.1 | 12.5 | 13 | 27 | >20 |
| KHM-3 | 6.3 | 6.3 | 25 | 50 | >50 | >50 | NT |
| KHM-4 | 6.3 | 3.1 | 6.3 | 12.5 | 20 | >50 | >20 |
| KHM-5 | 6.3 | 3.1 | 3.1 | 6.3 | >50 | >50 | NT |
| KHM-6 | 6.3 | 1.6 | 3.1 | 3.1 | 27 | >50 | >20 |
| KHM-7 | 3.1 | 1.6 | 3.1 | 3.1 | 12 | >50 | >20 |
| KHM-8 | 12.5 | 6.3 | 3.1 | 3.1 | NT | NT | NT |
| KHM-9 | 12.5 | 3.1 | 1.6 | 3.1 | NT | NT | NT |
| Pradimicin A | 12.5 | 1.6 | 0.8 | 3.1 | 10 | 23 | 0.02 |
| Pradimicin C | 25 | 0.8 | 3.1 | 3.1 | 14 | NT | NT |
| Pradimicin FA-1 | 6.3 | 0.8 | 1.6 | 1.6 | 18 | 27 | 0.26 |
| Pradimicin FA-2 | 6.3 | 1.6 | 1.6 | 3.1 | 7.4 | NT | 0.02 |

[1])Ca-4: *Candida albicans* A9540
Cn-2: *Cryptococcus neoformans* IAM 4514
Af-3: *Aspergillus fumigatus* IAM 2034
Tm-4: *Trichophyton mentagrophytes* #4329
[2])Water-solubility at neutral pH in phosphate buffered saline containing $Ca^{2+}/Mg^{2+}$.

We claim:

1. A process for preparing a 4'-cyanoamino pradimicin compound comprising contacting a 4'-amino or 4'-alkylamino pradimicin compound in a suitable organic solvent with a silylation reagent under conditions sufficient to activate the 4'-amino group or the 4'-alkylamino group, followed by contacting the activated compound with cyanogen bromide under conditions sufficient to form a silylated 4'-cyanoamino pradimicin derivative, followed by removal of the silyl moieties to result in formation of the desired 4'-cyanoamino derivative.

2. A process for preparing a 4'-nitroguanidino pradimicin compound comprising contacting a 4'-amino or 4'-alkylamino pradimicin compound in a suitable solvent with a silylation reagent under conditions sufficient to activate the 4'-amino group or the 4'-alkylamino group, followed by contacting the activated compound with N-nitro-S-methylisothiourea under conditions sufficient to form a silylated 4'-guanidino pradimicin, followed by removal of the silyl moities to result in formation of the desired 4'-guanidino pradimicin compound.

* * * * *